United States Patent [19]

Taguchi et al.

[11] Patent Number: 5,681,529
[45] Date of Patent: Oct. 28, 1997

[54] BIOLOGICAL FLUID ANALYZING DEVICE

[75] Inventors: Takayuki Taguchi; Shigeru Fujioka; Koichi Machida; Tadao Yamaguchi; Hajime Nakano, all of Sanda, Japan

[73] Assignee: Nihon Medi-Physics Co., Ltd., Japan

[21] Appl. No.: 518,281

[22] Filed: Aug. 23, 1995

[30] Foreign Application Priority Data

Aug. 25, 1994 [JP] Japan .................................. 6-224139

[51] Int. Cl.$^6$ .................................................. G01N 21/03
[52] U.S. Cl. .......................... 422/61; 422/102; 422/62; 436/808; 436/164
[58] Field of Search .................... 436/43, 45, 48–49, 436/808; 422/62, 63, 101, 164, 61, 102–104

[56] References Cited

U.S. PATENT DOCUMENTS

| | | |
|---|---|---|
| 3,630,957 | 12/1971 | Rey et al. . |
| 3,992,158 | 11/1976 | Przybylowicz et al. . |
| 4,477,575 | 10/1984 | Vogel et al. . |
| 4,753,776 | 6/1988 | Hillman et al. . |
| 4,756,884 | 7/1988 | Hillman et al. . |
| 4,814,282 | 3/1989 | Holen et al. . |
| 4,931,387 | 6/1990 | Yamao et al. . |
| 5,055,195 | 10/1991 | Trasch et al. . |
| 5,135,719 | 8/1992 | Hillman et al. . |
| 5,149,501 | 9/1992 | Babson et al. ............... 422/58 |
| 5,183,741 | 2/1993 | Arai et al. . |
| 5,227,310 | 7/1993 | Sakamoto et al. . |
| 5,230,866 | 7/1993 | Shartle et al. ............... 422/103 |
| 5,240,862 | 8/1993 | Koenhen et al. . |
| 5,399,486 | 3/1995 | Cathey et al. ............... 435/79 |

FOREIGN PATENT DOCUMENTS

| | | |
|---|---|---|
| 0194502 | 9/1986 | European Pat. Off. . |
| 0 212 314 | 3/1987 | European Pat. Off. . |
| 0283613 | 9/1988 | European Pat. Off. . |
| 0487068 | 5/1992 | European Pat. Off. . |
| 1231897 | 9/1989 | Japan . |
| 2208565 | 8/1990 | Japan . |
| 4208856 | 7/1992 | Japan . |
| 5273207 | 10/1993 | Japan . |
| 1440464 | 6/1976 | United Kingdom . |

OTHER PUBLICATIONS

Pavon et al, "Universal sandwich membrane cell . . . ", Analytical Chemistry, 1992, vol. 64, pp. 923–929.

*Primary Examiner*—Lyle A. Alexander
*Attorney, Agent, or Firm*—Cushman Darby & Cushman Intellectual Property Group of Pillsbury Madison & Sutro, LLP

[57] ABSTRACT

The biological fluid analyzing device for analyzing biological fluid by measuring optical characteristics of a sample has a sample receiving port 1 and a pump connection port 5. Between the sample receiving port 1 and the pump connection port 5, the analyzing device has either a combination of at least one sample-treating chamber 2a, 2b, 2c and at least one optical-measuring chamber 3a, 3b, or a combination of at least one sample-treating chamber, at least one optical-measuring chamber and at least one waste liquid reservoir 4. The sample receiving port 1 is connected with one sample-treating chamber; the pump connection port 5 is connected with a pathway 6 or waste liquid reservoir 4; and the sample-treating chamber and optical-measuring chamber are interconnected with the pathway, or the sample-treating chamber, optical-measuring chamber and waste liquid reservoir are interconnected with the pathway. This construction allows a series of reaction steps to be performed without being affected by physical properties of a liquid sample and thereby assures high level of precision in analyzing the liquid sample. This construction also enables measurements to be made easily.

25 Claims, 11 Drawing Sheets

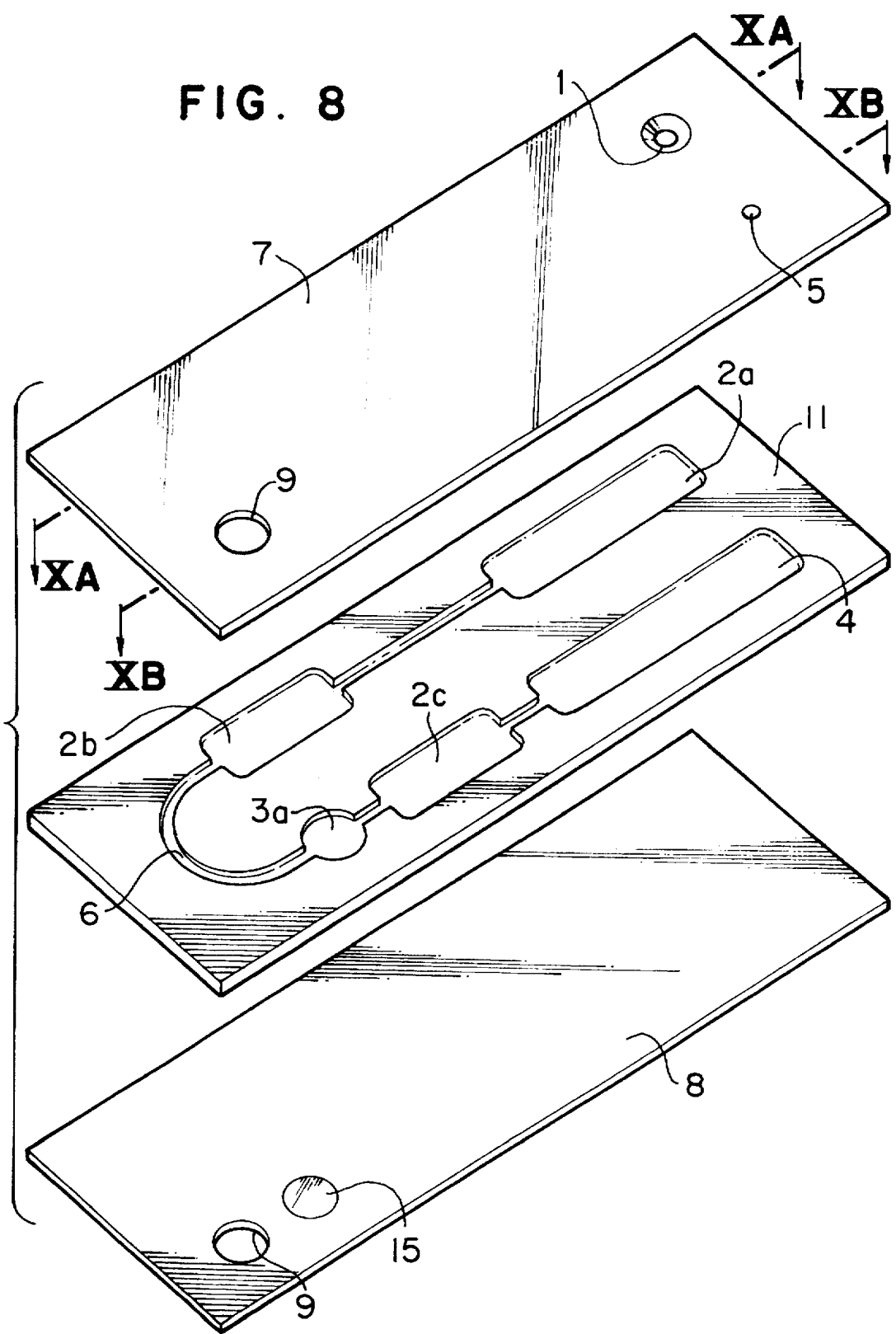

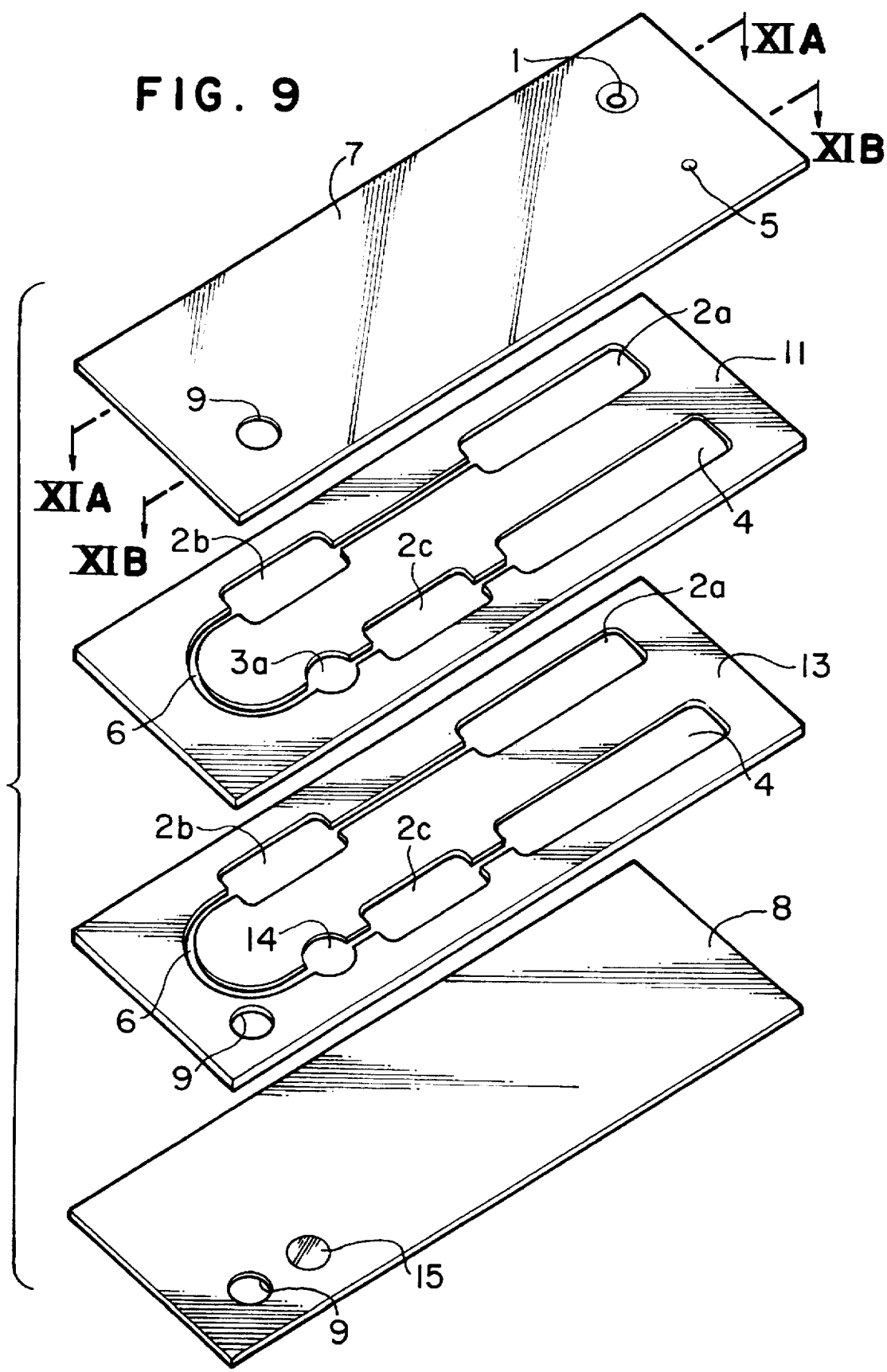

BIOLOGICAL FLUID ANALYZING DEVICE

BACKGROUND OF THE INVENTION

1. Field of the Invention

The present invention relates to a disposable analyzing device and a method using such a device for a simple analysis of the components of biological fluid such as glucose, triglyceride, uric acid, cholesterol and HbAlc.

2. Prior Art

A disposable dry analyzing device, which can take measurements easily, has found wide use in the analysis of the components of biological fluid, particularly for humans.

An early type of the simple analyzing device is what is generally called a "test paper," which is made by impregnating a filter paper with a reagent for reaction and then drying the impregnated filter paper. For analysis, the test paper is immersed in a sample and, after a predetermined time, the color of the filter paper surface is visually checked. This method, however, has a limit of precision dictated by unevenness of the filter paper itself and therefore has mainly been used for detecting the (Half quantitative assay) components in urine.

Attempts have also been made to utilize the test paper for analysis of components in blood. Because the blood analysis requires additional processes such as washing and/or blotting for removing blood cells, and because the accuracy problem due to unevenness of filter paper itself cannot be overcome, the precision attained is not satisfactory despite the use of a dedicated apparatus.

Disclosed for the analysis of in-blood components that requires high level of precision is a "test film" (Japan Patent Publication No. 49-33800) that is applied for simplified measurement of blood sugar. The "test film" is made by applying a reagent for reaction, together with a reagent carrier called a binder, to a plastic film and then drying them. Although it overcomes the unevenness of the filter paper, an early type of the test film requires a step of wiping off blood cells remaining on the test film. This brings in a problem of variations among persons who take measurements. As a result, a sufficiently high level of accuracy was not attained with the test film.

In a multi-layer test film using a lamination technology such as photographic film technology, when whole blood is applied to the film, the corpuscle component is removed by a corpuscle removing layer, with only the plasma component of the blood moving into a reagent layer where it reacts with the reagent and produces a color dye. Next, a light is projected upon the sample from the opposite side of the sample applying section, and the intensity of light reflected from a light reflection layer provided between the reagent layer and the corpuscle removing layer is measured. Although it has achieved a level of accuracy that could not be realized with the conventional dry analyzing device, this test film has a drawback that, because the section for radiating a measuring beam overlaps a separated area where corpuscles exist, the analysis precision is not free from optical effects of the overlapped sections and moreover from effects of physical properties such as viscosity of the sample (Japan Patent Laid-Open No. 5-273207, 2-208565 and Publication No. 53-21677).

The structure and the precision of test pads have made remarkable improvements in recent years but not to an extent that satisfies the requirements of clinical examinations. One of the reasons for this is that the carrier for reagent used in the dry analyzing device has a matrix structure. That is, when a liquid sample spreads itself into the matrix, differing physical properties of the liquid sample such as viscosity may result in variations in the rate and amount of infiltration into the matrix. This may change the amount of sample per unit area and the degree of swelling of the carrier matrix, which in turn changes the thickness of layer, causing variations in an optical signal at the time of measurement and thereby degrading the accuracy of the measurement.

In order to prevent deterioration of precision due to variations in the amount of the sample and the thickness of the test pads caused by differing physical properties of the liquid sample, a test cassette is disclosed, in which reagent is placed in a plastic container (Japanese Patent Laid-Open No. 60-238761). In this test cassette, the sample is successively transferred by centrifugal force to small chambers in the cassette assigned with roles corresponding to respective layers of the multi-layer test film. Measurement is made by a optical-measuring cell. Because the cell has a fixed predetermined thickness, measurements can be made with high precision. The test cassette, however, has the drawback that because a centrifugation process is required, the apparatus for measuring the test cassettes becomes large and produces noise and the production of the cassette having a plurality of small chambers is costly.

An analyzing device utilizing capillary action, whereby liquid is absorbed, is disclosed in Japan Patent Laid-Open No. 62-129759. This device uses capillary force in moving the liquid to a plurality of chambers. The liquid transfer control using the capillary force is performed by an energy-orienting ridge provided in a flow path and by an open-close means at an inlet. Although it offers the ability to determine the amount of liquid by the capacity of the chamber provided in the capillary flow path, this method has a drawback that because the speed of transfer depends on the viscosity and surface tension of the liquid, the processing time cannot be controlled precisely. Another problem is that the fabrication is complex because this method requires the energy-orienting ridge and surface machining for control of capillary flow.

In these dry analyzing devices, if a biological fluid is used as a sample without being diluted, the possibility cannot be ruled out that glucose, cholesterol and triglyceride in the sample may not be fully oxidized by the oxidizing enzymes because of lack of oxygen dissolved in the sample, stopping the reaction.

SUMMARY OF THE INVENTION

Under the circumstances mentioned above, it is the object of this invention to provide a biological fluid analyzing device and a method using such a device, which can attain a high level of precision in analyzing a liquid sample through a series of reaction and measuring steps without being affected by physical properties of the sample and which allows measurements to be made easily.

To achieve the above objective, the present invention has been accomplished through vigorous research. A first aspect of this invention is characterized by a biological fluid analyzing device for making a biological fluid analysis by measuring optical characteristics of a treated sample, and also by a biological fluid analyzing method using such a device. The biological fluid analyzing device comprises: a sample receiving port 1; a pump connection port 5; between the sample receiving port 1 and the pump connection port 5, either a combination of at least one sample-treating chamber 2a, 2b, 2c and at least one optical-measuring chamber 3a, 3b or a combination of at least one sample-treating chamber, at least one optical-measuring chamber and at least one waste liquid reservoir chamber 4, and a pathway 6 connecting all these chambers. The biological fluid analyzing method using such a device comprises the steps of: applying a sample to the sample receiving port; moving the sample in a predetermined order by suction or pressure from a pump connected to the pump connection port; treating the sample with reagents applied to the sample-treating chamber and to the sample; moving the treated sample to the optical-measuring chamber provided near the sample-treating chamber; and measuring optical characteristics of the treated sample.

A second aspect of this invention is that the above-mentioned biological fluid analyzing device further includes a gas-permeable film 17 and an air layer 18 isolated by the gas-permeable film 17, both provided in at least one sample-treating chamber 2a, 2b, 2c.

A third aspect of this invention is characterized by a blood corpuscle separating method. The blood corpuscle separating method uses the biological fluid analyzing device which further includes a blood corpuscle separating portion that comprises: a filter 20 through which blood corpuscles cannot pass and an air hole 21 formed as required in the pathway 6 at a point following the filter, whereby the filter is installed under the sample receiving port 1 with its outer periphery securely held by a stepped retainer portion 19. Using this analyzing device, the blood corpuscle separating method performs the steps of applying whole blood onto the sample receiving port 1, drawing in the sample by suction from the pump connection port 5, and separating the blood corpuscles through the blood corpuscle separating portion.

With this construction, the sample, as it is transferred from one chamber to another, undergoes a series of predetermined processes including preprocessing such as blood corpuscle separation, reaction process, reaction stop process and optical-measuring process to produce data on the measured light representing the optical characteristics of the sample. Because the liquid sample is transferred by mechanical means such as pump, not only is the analysis free from influences of physical properties of the sample such as viscosity but also the flow of liquid can be controlled precisely. Further, this construction allows the sample to be moved in the reverse direction easily. The gas-permeable film and the air layer supply oxygen to help the oxidizing enzyme. Furthermore, because the biological fluid analyzing device is used as a disposable device that can be discarded after use, it is advantageous in terms of ease of use and cleanliness.

BRIEF DESCRIPTION OF THE DRAWINGS

FIG. 8 is a perspective view showing the process of assembling the biological fluid analyzing device of FIG. 4;

FIG. 9 is a perspective view showing another process of assembling a modified version of the biological fluid analyzing device of FIG. 4;

DETAILED DESCRIPTION OF THE PREFERRED EMBODIMENTS

Embodiments of the biological fluid analyzing device of this invention are described by referring to the accompanying drawings.

Figure 3:
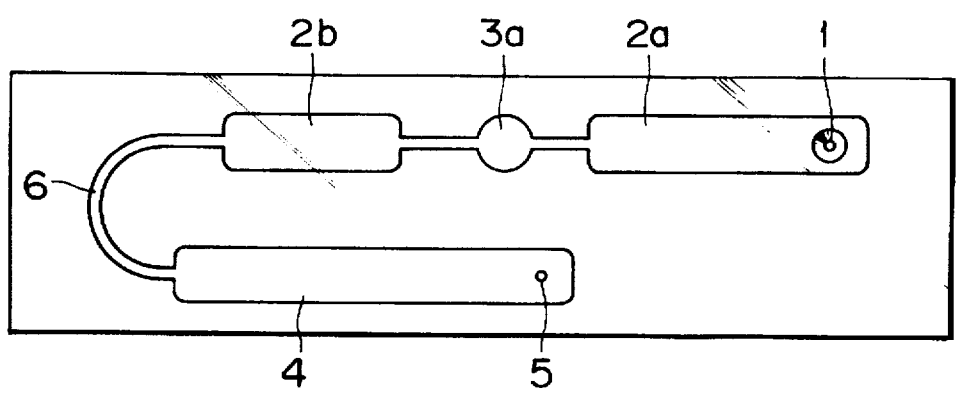
FIG. 3 is a plan view showing a second embodiment of a biological fluid analyzing device according to the present invention.
Figure 4:
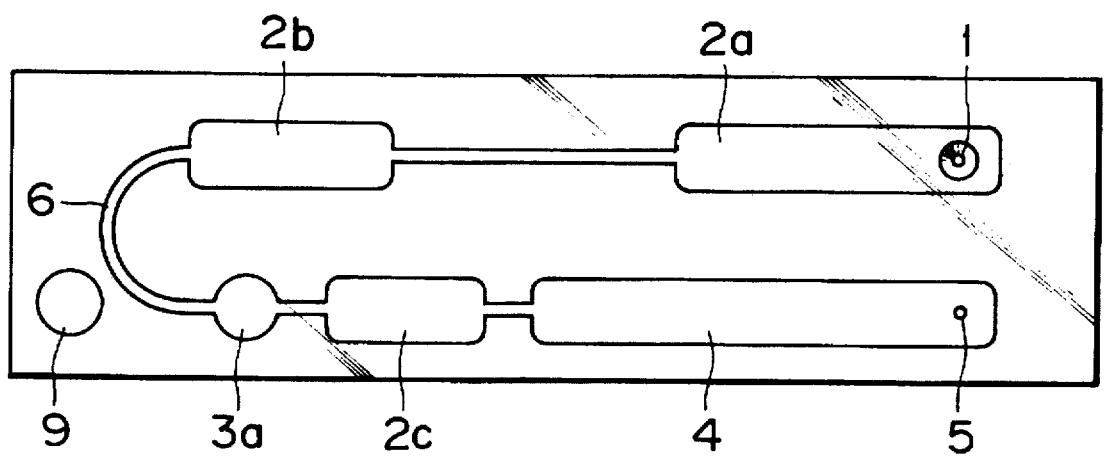
FIG. 4 is a plan view showing a third embodiment of a biological fluid analyzing device according to the present invention.
Figure 5:
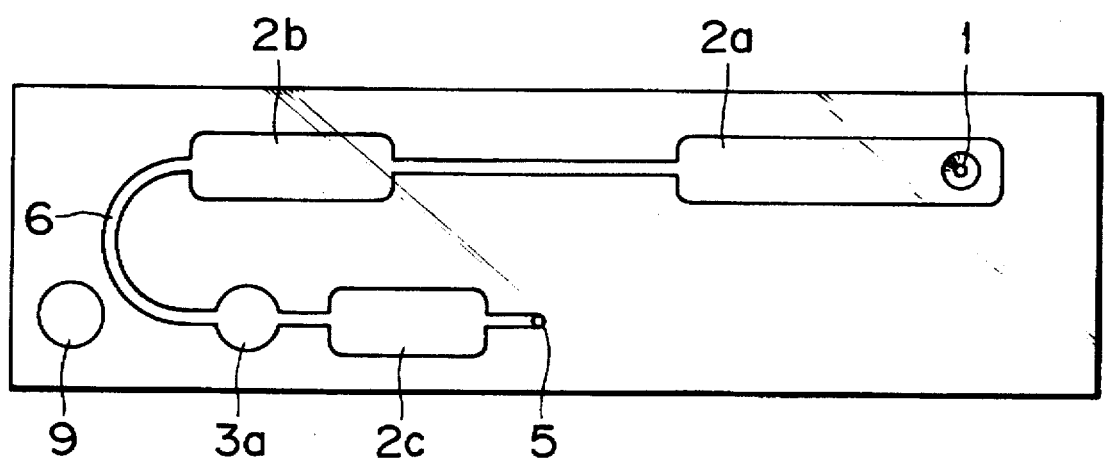
FIG. 5 is a plan view showing a fourth embodiment of a biological fluid analyzing device according to the present invention.

Example configurations of the biological fluid analyzing device are shown in FIGS. 1 to 11. The biological fluid analyzing device shown in each of these figures has a sample receiving port 1, a pump connection port 5 and, between these ports, a combination of at least one sample-treating chamber 2a, 2b, 2c and at least one optical-measuring chamber 3a, 3b or a combination of at least one sample-treating chamber, at least one optical-measuring chamber and at least one waste liquid reservoir 4, and also a pathway 6, which can be optionary a capillary, connecting all these. The number of sample-treating chambers and the optical-measuring chambers can be increased or reduced as required. The sample-treating chambers may be modified to work as optical-measuring chambers as well. The waste liquid reservoir may be added as necessary depending on the items to be measured. FIG. 5 shows a structure, in which the pathway 6 is directly connected to the pump connection port without providing a waste liquid reservoir.

Figure 6:
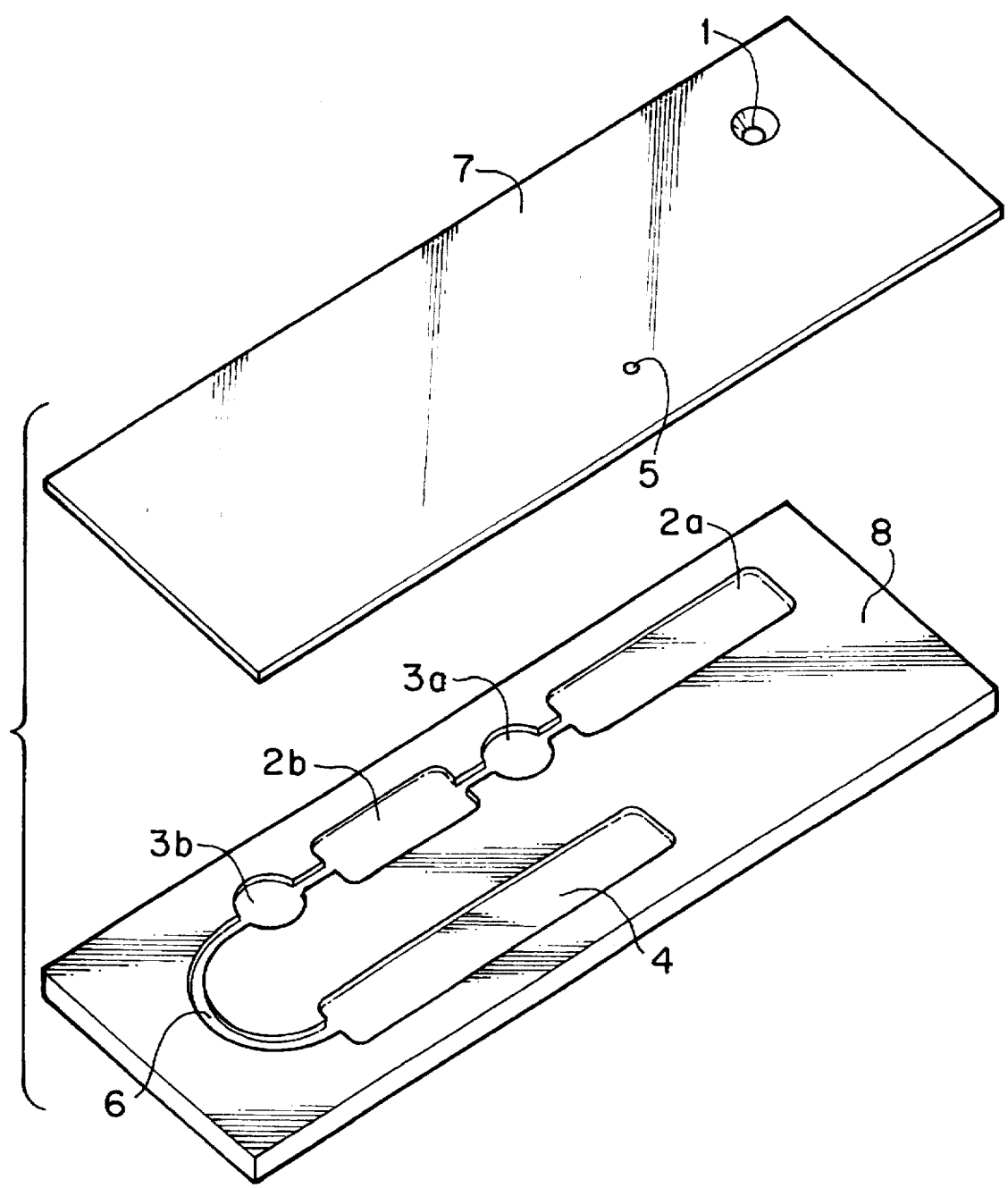
FIG. 6 is a perspective view showing the process of assembling the biological fluid analyzing device of FIG. 1.

The biological fluid analyzing device of this invention includes an upper plate 7 and a lower plate 8. The upper plate 7 is formed with the sample receiving port 1 and the pump connection port 5. The sample-treating chamber and the optical-measuring chamber, or the sample-treating chamber, the optical-measuring chamber and the waste liquid reservoir, and the pathway connecting these may be provided either in the upper plate or in the lower plate, as long as they are formed when the upper and lower plates are combined into the biological fluid analyzing device. The biological fluid analyzing device of FIG. 6 shows that the lower plate has the sample-treating chamber, the optical-measuring chamber and the waste liquid reservoir.

There are no restrictions on the size, shape or material of the biological fluid analyzing device, and the only requirement is that the device be so sized as to be accommodated in common easy operational clinical test apparatuses. Preferable materials include such plastics as polyester, polyethylene, polypropylene, polystyrene, polyvinyl chloride and ABS. Desired shapes of the device can be obtained easily if these materials are used. The use of a light-transmissive material allows the measurement of light to be performed easily.

The device needs only to have a capacity enough to receive 10–50 μl of biological fluid, such as whole blood, as a sample and to allow injection of a sample-treating reagent in each sample-treating chamber. The waste liquid reservoir is preferably larger in volume than the sample received so that the biological fluid after having been subjected to measurement is not sucked into the pump. The pathway which connects these chambers and reservoir should be as small as possible, as long as such movement as drawing or compressing by a pump is not hindered. The pump moves the sample by drawing out or compressing air present inside the device and may use a microsyringe.

Measurement of optical characteristics may be made by applying light having a particular wavelength of, for instance, 300–800 nm to the sample e.g. by use of a light emitting diode, tungsten lamp, xenon flashlamp or mercury lamp. Either transmitted light or reflected light may be applied to the sample. When transmitted light is measured, the optical-measuring chamber is made of a optical-transmissive material; and when reflected light is used, either the upper or lower surface of the optical-measuring chamber is made of a light-reflective material with the remainder formed of a light-transmissive material. The light-reflective material is, for instance, a plastic film mixed with white pigment such as titanium dioxide. In more concrete terms, the biological fluid analyzing device may have formed of a light-reflective material at least a portion of the upper plate that corresponds to the optical-measuring chamber and have formed of a light-transmissive material at least a portion of the lower plate that corresponds to the optical-measuring chamber; another device may have formed of a light-transmissive material at least a portion of the upper plate that corresponds to the optical-measuring chamber and have formed of a light-reflective material at least a portion of the lower plate that corresponds to the optical-measuring chamber; and still another device may have formed of a light-transmissive material at least portions of the upper and lower plate that correspond to the optical-measuring chamber.

Figure 1:
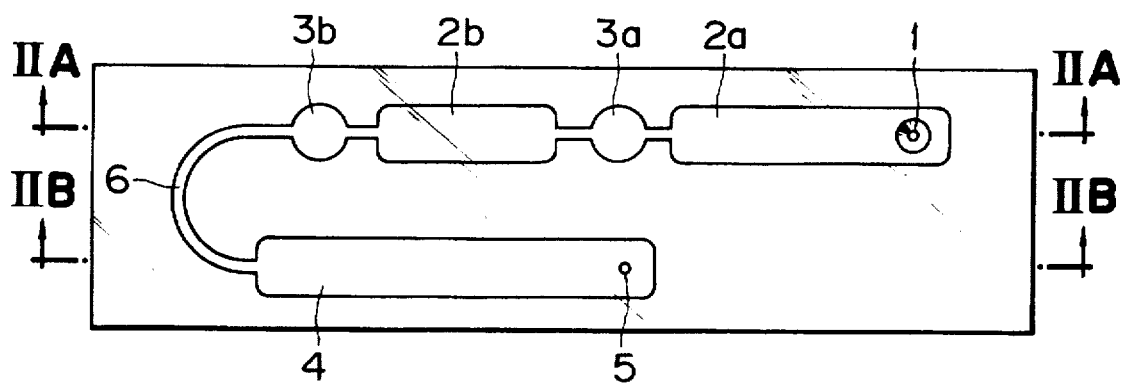
FIG. 1 is a plan view showing a first embodiment of a biological fluid analyzing device according to the present invention.
Figure 2A:
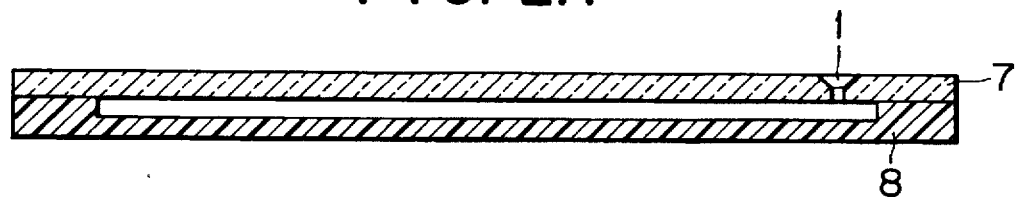
FIG. 2(a) is a cross section taken along the line IIA—IIA of the biological fluid analyzing device of FIG. 1.
Figure 2B:
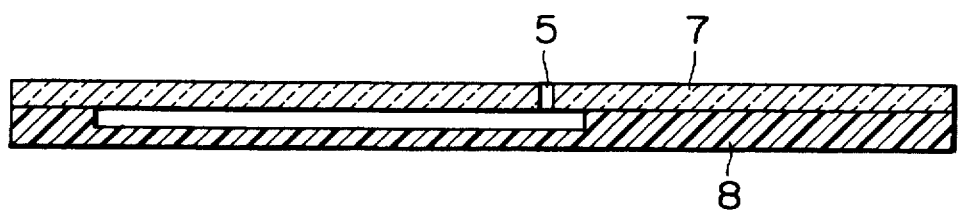
FIG. 2(b) is a cross section taken along the line IIB—IIB of the biological fluid analyzing device of FIG. 1.

Now, the biological fluid analyzing devices shown in FIGS. 1 and 2 are explained.

The sample is applied to the sample receiving port 1 and then drawn into the interior of the device by drawing the air out of the device by a pump (not shown) connected to the pump connection port 5. In the sample-treating chamber 2a, substances that may hinder reaction with an object substance or cause measurement errors are removed from the sample. Removal of interfering substances for each measurement item and of intrinsic substances may be achieved by method known in this field. For example, ascorbic acid, a typical interfering substance for biochemical items, may be removed by preparing one of the sample-treating chambers as an interfering substance removing area, such as by applying a liquid containing ascorbate oxidase and drying beforehand. Here, it is also possible to remove any intrinsic ammonia that may cause background interference when measuring blood urea nitrogen (BUN) and creatinine. Then, in the optical-measuring chamber 3a the blank value of the optical characteristic of the sample is measured; in the sample-treating chamber 2b the sample is made to react with a reagent already applied in this chamber; and after this, the optical characteristics are measured in the optical-measuring chamber 3b. Measurement of optical characteristics in the optical-measuring chambers 3a, 3b is done either by measuring the transmitted light with the optical-measuring chamber disposed between the light source or the light-receiving section or by making one of the upper or lower surfaces of the measuring section light-reflective, using this as a reflector and measuring the reflected light as by an integrating sphere from the opposite side.

A sample-treating chamber may also be used as a reaction stop cell. Because enzymes act as catalysts, the enzyme continues to react with the substrate in the sample under appropriate conditions as long as there is substrate present. Hence, stopping the reaction after elapse of an appropriate time is advantageous not only for shortening the time but also for reducing the amount of substrates consumed for reaction. When this invention is applied to an apparatus that can take measurements of a plurality of analyzing devices at one time, the measurement timings may overlap depending on the combination of the devices. In such a case, by stopping the reaction by this reaction stop cell, measurement can be taken at any desired time. Any of the sample-treating chambers can be made a reaction stop cell by putting in it an enzyme reaction inhibitor to prevent reaction in a reaction liquid from endlessly continuing, an acid, alkali or buffer liquid to adjust the pH of the reaction liquid into a non-reactive pH region.

Figure 7:
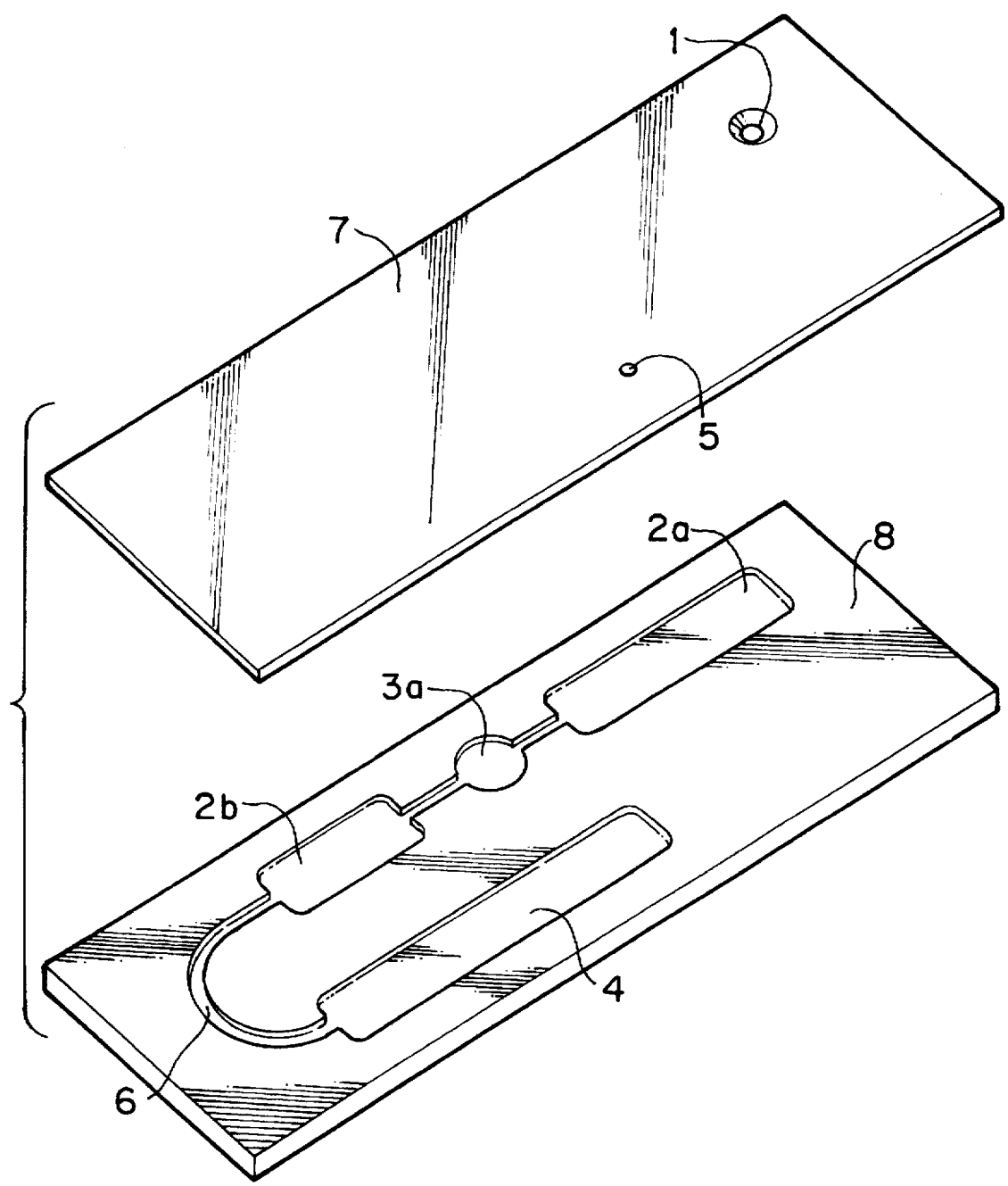
FIG. 7 is a perspective view showing the process of assembling the biological fluid analyzing device of FIG. 3.

FIG. 3 and FIG. 7 are a plan view and a perspective view, respectively, showing a second embodiment of 10 this invention. What differs from FIG. 1 is that only one optical-measuring chamber 3a is provided. In this analyzing device, the blank value of the optical characteristic of the sample not yet reacted is measured in the optical-measuring chamber 3a. The sample is then moved to the sample-treating chamber 2b where it is reacted with a reagent to produce a color. The colored-sample liquid is transferred by the pump back to the optical-measuring chamber 3a again where the optical characteristic is measured once more. This method uses only one optical-measuring chamber and thus can eliminate errors between different optical-measuring chambers and reduce the cost of making a dedicated measuring apparatus.

FIG. 4 shows a third embodiment. By making the sample-treating chamber 2a following the sample receiving port 1 an area for separating and removing only the corpuscle component from whole blood, it is possible to use whole blood as a sample.

Figure 10A:
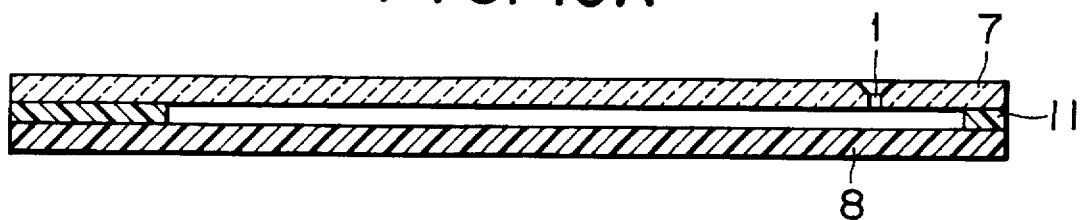
FIG. 10(a) is a cross section taken along the line XA—XA in the biological fluid analyzing device of FIG. 8.
Figure 10B:
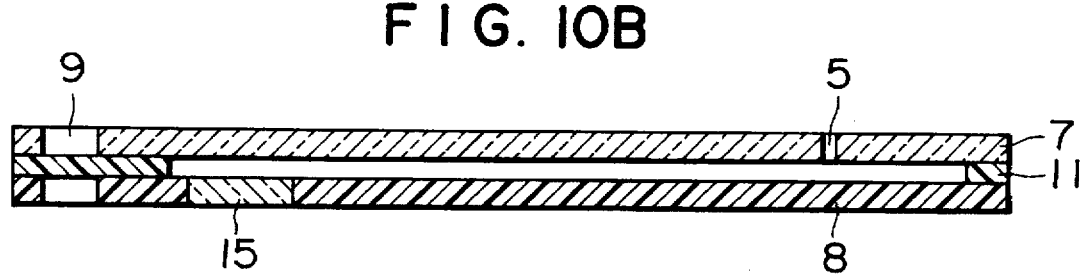
FIG. 10(b) is a cross section taken along the line XB—XB in the biological fluid analyzing device of FIG. 8.

FIG. 8 shows how the biological fluid analyzing device of this invention, that of FIG. 4, using a spacer is assembled. FIG. 10 shows a cross section of the device of FIG. 8. A spacer 11 made of a plastic film which has sample-treating chambers and optical-measuring chambers in the form of through-holes is held between an upper plate 7 and a lower plate 8. The plastic film 11 may be flexible and may be made of polyester. That is, the spacer 11 clamped between the upper plate 7 and the lower plate 8 has formed as through-holes therein, between the sample receiving port 1 and the pump connection port 5, a combination of at least one sample-treating chamber, namely three, 2a, 2b, 2c and an optical-measuring chamber 3a, (or a combination of at least one sample-treating chamber), optical-measuring chamber and waste liquid reservoir 4, and also a pathway 6 connecting all these. The sample receiving port 1 and the pump connection port 5 may be formed either in the upper plate 7 or lower plate 8, or may be formed in the spacer portion at the side surface or edge of the device. An optical-measuring window 15 may be formed by making both the upper and lower plates light-transmissive or making one of them light-reflective so that transmitted or reflected light can be measured.

The sample such as whole blood, after being applied onto the sample receiving port 1, is led into the analyzing device by a pump (not shown) connected to the pump connection port 5 drawing air out of the device. The sample is separated into components and corpuscle components removed in the sample-treating chamber 2a, with only the plasma (blood serum) component transferred to the sample-treating chamber 2b, which is an interfering substance eliminating region.

Separating blood cells from the whole blood may be achieved by attaching a glass filter or a matrix impregnated with lectin to the sample-treating chamber 2a to make the chamber a corpuscle-separating region. Alternatively, the segregation capability may be provided or enhanced by providing a filter below the sample receiving port. That is, the biological fluid analyzing device may have below the sample receiving port a corpuscle-separation region made of a filter that blocks passage of blood cells and which is held at its periphery by a retainer 19 e.g. having a step. Although there is no restriction on the pore size of the filter, the filter pore size should preferably be such as will pass plasma but not blood cells. Among preferred filters are a membrane filter and a glass filter that use synthetic resin, such as a cellulose acetate filter and a polyfluoroethylene filter. It is more desirable to use a membrane filter which has inclined pores with pore sizes differing between the upper and lower surfaces.

Figure 16:
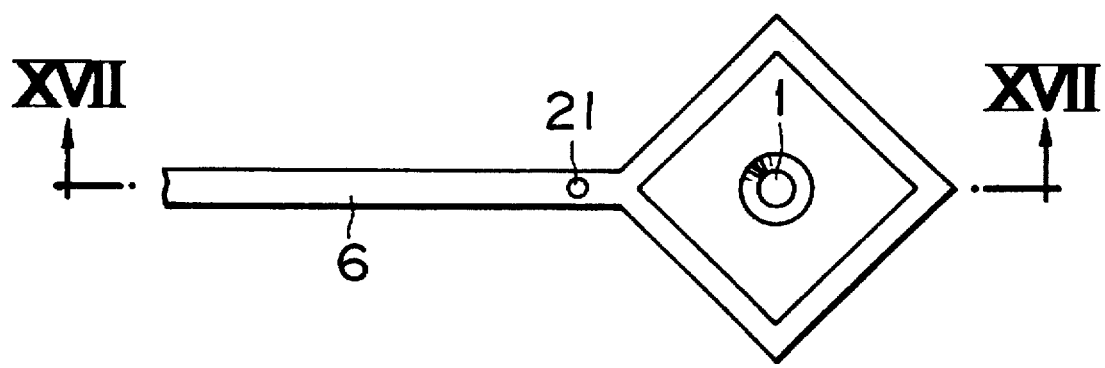
FIG. 16 is a plan view of a sample receiving port having a filter at the bottom.
Figure 17:
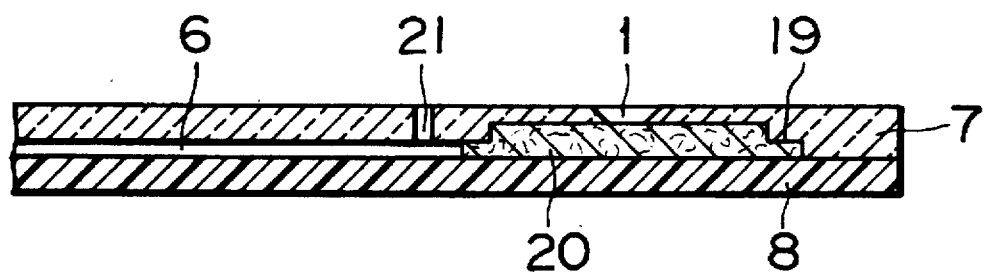
FIG. 17 is a cross section taken along the line XVIIA—XVIIA in the sample receiving port of FIG. 16.

FIG. 16 and FIG. 17 show the structure of a corpuscle-separating portion of the analyzing device, which consists of a filter with a corpuscle-separating function installed below the sample receiving port and an air hole 21 formed in the pathway at a point following the filter. FIG. 16 is a plan view of the sample-receiving port as seen from above and FIG. 17 is a cross section of the same as seen from the front.

For blood cell separation, the whole blood is applied onto the sample-receiving port 1 and allowed to penetrate into the filter. Air is drawn out from the pump-connection port 5 to cause the plasma to seep through the outer periphery of the filter and flow in the pathway 6. The plasma can then be subjected to a series of measurements. If a reagent, which reacts with an object component in the plasma to produce a color, is supplied into the pathway and then dried beforehand, it is possible to determine the concentration of an object substance while drawing in the plasma.

When the filter 20 having a corpuscle-separating capability is provided under the sample-receiving port 1, it is one of the recommended practices to form an air hole 21 in the pathway 6 at a point following the filter, as shown in FIGS. 16 and 17. When blood cells are to be separated, this air hole 21 is closed to enable the plasma to be drawn in by the pump. When moving the sample thereafter, the air hole is opened to make the flow of plasma smooth.

The retainer portion 19 holds the outer periphery of the filter and is designed not only to clamp the filter between the upper and lower plates but also to make small the pores in the clamped portion of the filter and thereby prevent leakage of blood cells improving the effectiveness of separation between blood cells and plasma. The retainer portion has two steps that contribute to firm holding of the outer periphery of the filter. The height of the portion where the filter is installed and the height of the portion that holds the filter can be adjusted according to the filter used.

The filter-installation portion may take any desired shape, but considering the ease with which the sample flows into the pathway, ease of installing the filter in place and ease of machining, a circle or square is most preferred. As to the shape of the sample-receiving port to which the whole blood is applied, a circular or square one is preferable from the viewpoint of ease of use and machining.

In FIG. 8, the sample-treating chamber 2b into which the plasma was transferred acts as an interfering substance removing region, which eliminates substances that interfere with the reaction with the object substance or which can cause measurement errors. Removal of interfering substances for each measurement item and of intrinsic substances may make use of methods known in this field. For example, ascorbic acid, a typical interfering substance for biochemical items, may be removed by installing a matrix containing ascorbate oxidase in the interfering substance removing region or by applying a liquid containing ascorbate oxidase onto the interfering substance removing region and drying it.

It is also possible in this chamber to remove any intrinsic ammonia that may cause background interference when measuring blood urea nitrogen and creatinine. Then, in the optical-measuring chamber 3a the blank value of the sample is measured. In the sample-treating chamber 2c the liquid sample is reacted and then transferred back to the optical-measuring chamber 3a where the optical characteristic after the reaction is measured. Measurement of optical characteristics in the optical-measuring chamber 3a is done either by measuring the transmitted light with the optical-measuring chamber 3a disposed between the light source and the light-receiving section or by making the upper plate 7 light-reflective, using this as a reflector and measuring the reflectivity as by an integrating sphere from the lower plate 8 side.

In this embodiment using the spacer, because the thickness of the optical-measuring chamber 3a is equal to that of the spacer, it is possible to adjust the light path length in the optical-measuring chamber by measuring the optical characteristic of the spacer through an optical characteristic correction reference window 9 located close to the optical-measuring chamber 3a to determine the thickness of the spacer and by taking the thickness of the spacer as the thickness of the optical-measuring chamber in adjusting the optical path length. The reference window for correcting the optical characteristic need not be formed as a window but need only be secured as a region in which to measure the optical characteristics of the spacer as long as it is located near the optical-measuring chamber. By allowing the thickness of the optical-measuring chamber to be corrected in this way, the analyzing device can easily be adapted for individual samples.

Figure 11A:
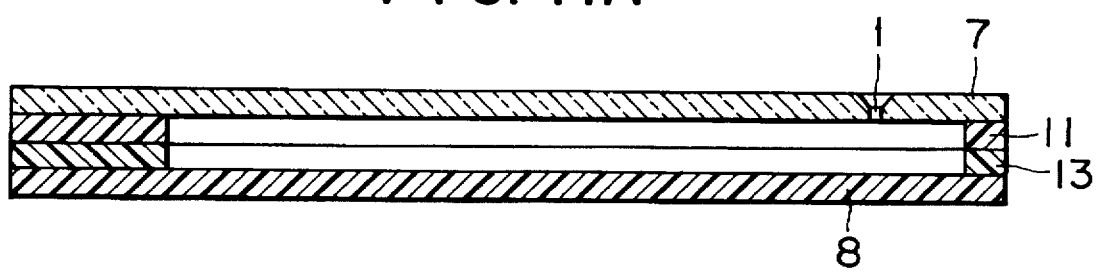
FIG. 11(a) is a cross section taken along the line XIA—XIA in the biological fluid analyzing device of FIG. 9.
Figure 11B:
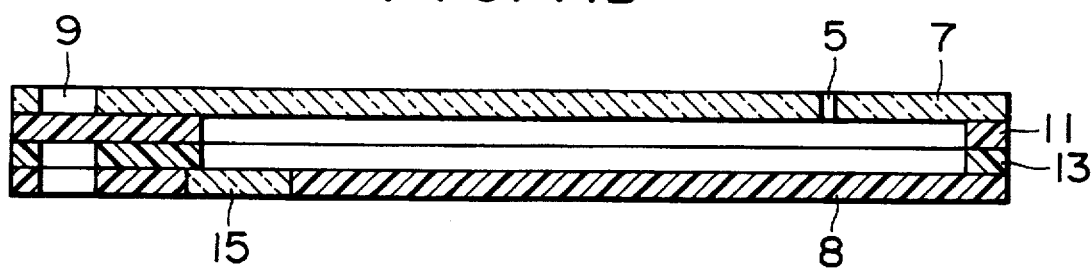
FIG. 11(b) is a cross section taken along the line XIB—XIB in the biological fluid analyzing device of FIG. 9.
Figure 12:
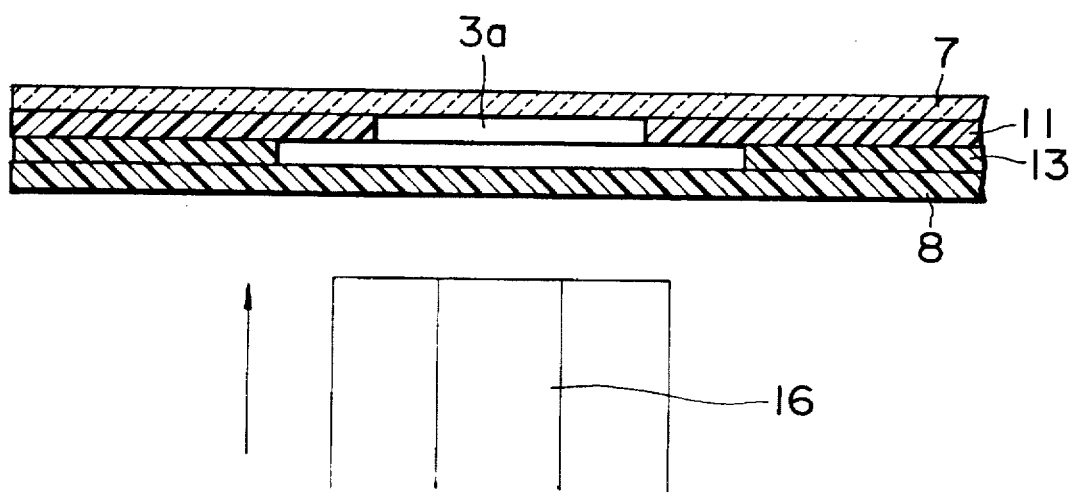
FIG. 12 is a cross section showing an optical-measuring chamber of the biological fluid analyzing device using an adjuster.
Figure 13:
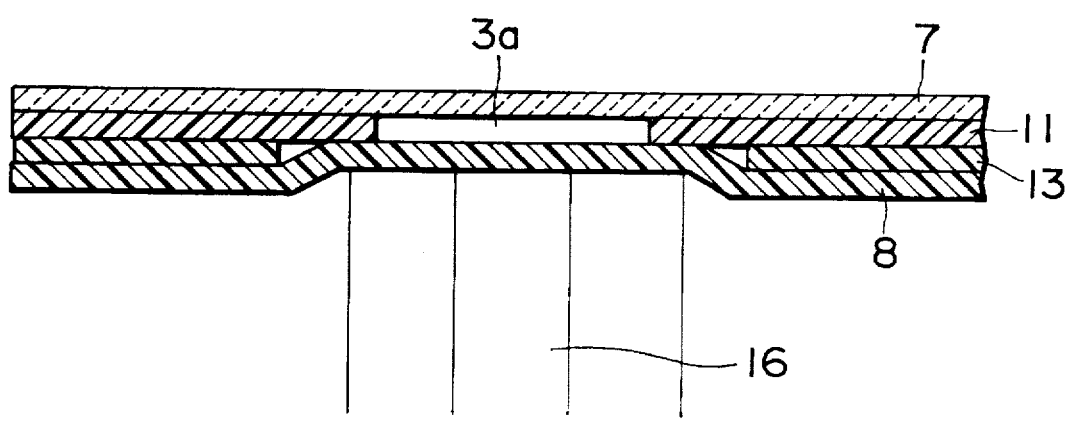
FIG. 13 is a cross section showing a optical-measuring chamber of the biological fluid analyzing device using an adjuster when a beam of light is measured.

Further, depending on the measurement items, the thickness of the optical-measuring chamber may need to be reduced because the concentration of an object substance in the sample may be too high and the light-absorbing capability of the colored liquid thus may be too high. In such a case, an adjuster 13 may be provided, which can reduce the thickness of only the optical-measuring chamber, as shown in FIGS. 9, 12 and 13. The adjuster 13 may be flexible and may be made of polyester. FIG. 11 shows a cross section of the present biological fluid analyzing device having the adjuster above. That is, the biological fluid analyzing device has a spacer and an adjuster under the spacer, both clamped between the upper plate and the lower plate. The spacer has formed as through-holes a combination of sample-treating chamber and optical-measuring chamber or a combination of sample-treating chamber, optical-measuring chamber and waste liquid reservoir, and a pathway connecting all these. The adjuster arranged beneath the spacer has formed as through-holes a combination of sample-treating chamber and optical-measuring chamber or a combination of sample-treating chamber, optical-measuring chamber and waste liquid reservoir, and a pathway connecting all these, with the optical-measuring chamber formed greater than that of the spacer. The biological fluid analyzing device may further include an optical characteristic correction region 9.

FIGS. 12 and 13 show a part of the cross section of the biological fluid analyzing device of FIG. 9. The adjuster 13 has the same shape as the spacer except for the optical-measuring chamber 3a and the optical characteristic correction reference window 9. The optical-measuring chamber in the adjuster is larger than that of the spacer. When the optical-measuring chamber of the adjuster is pressed by the light source 16 or light-receiving portion from the lower plate side, the lower plate comes into contact with the spacer (FIG. 13), so that the light path length at the time of measurement becomes equal to the thickness of the spacer 11. Further, because the portion 9 of the adjuster 13 corresponding to the reference window 9 is a through-hole, the adjuster cannot be seen from the reference region. The adjuster therefore does not affect the measurement of the spacer thickness.

Figure 14:
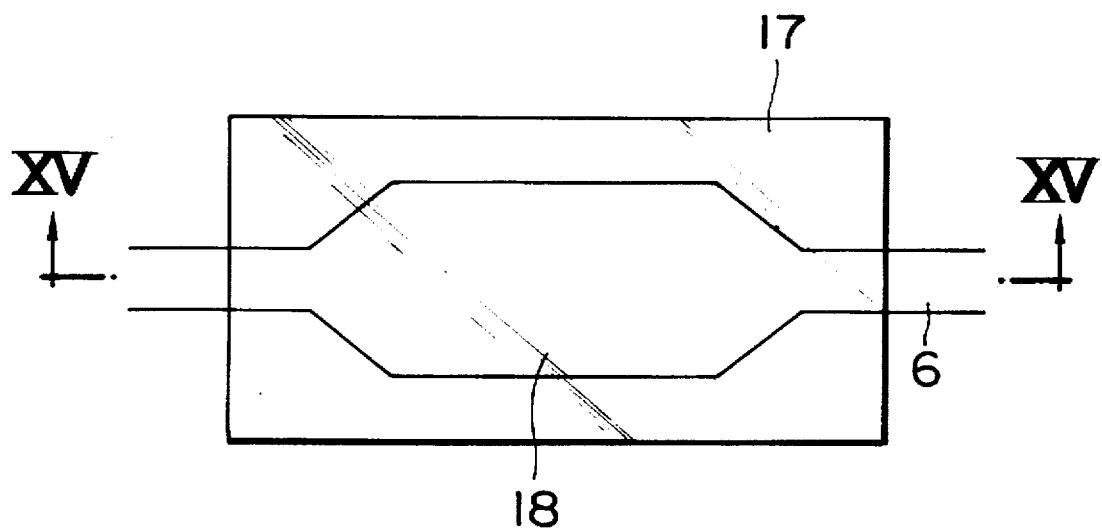
FIG. 14 is a plan view showing an oxygen supplying layer.
Figure 15:
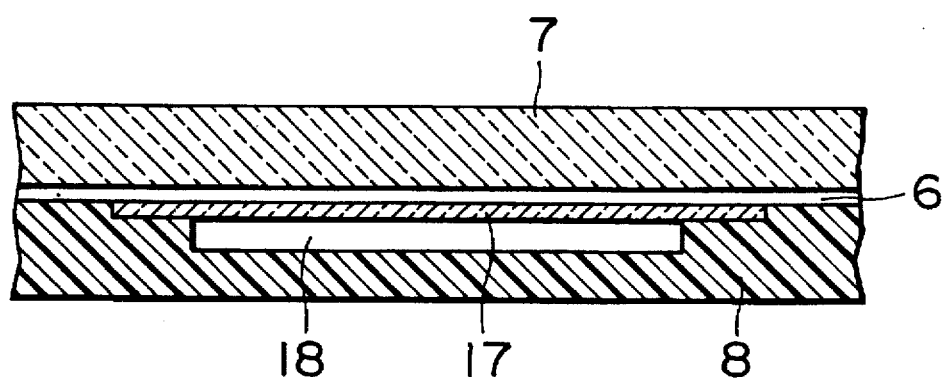
FIG. 15 is a cross section taken along the line XVA—XVA in the oxygen supplying layer of FIG. 14.

FIG. 14 is a plan view of an oxygen-supply portion of the analyzing device as seen from above. FIG. 15 is a cross section of the same as seen from the front. This analyzing device consists of an upper plate 7 and a lower plate 8. In FIG. 15, the upper plate is formed with a pathway 6, and the lower plate with a gas-permeable film 17 and an air layer 18. The gas-permeable film and the air layer may be provided in the upper plate or in both upper and lower plates with the pathway interposed therebetween.

The gas-permeable film is preferably porous and hydrophobic and may use, for example, nonwoven fabric and membrane filter formed of polytetrafluoroethylene (PTFE), cellulose-mixed polyethylene, polyfluorovinylidene and polycarbonate.

Example measurements using the analyzing device of this invention are presented in the following.

(EXAMPLE 1)

Measurement of uric acid

Uric acid was measured by using the analyzing device of this invention shown in FIG. 1. Measurement of optical characteristic was made by an apparatus that uses a tungsten lamp as a light source and which has a lens, a slitter and an interference filter installed between the light source and a light detector. The apparatus can convert the output of the detector into the optical density. This apparatus also permits display of concentration according to a calibration curve defined separately. In the succeeding examples, too, the optical characteristics were measured by this apparatus.

Sizes of regions in the analyzing device and reagents used:

Height of pathway and chambers region: 200 μm

Volume of sample-treating chamber 2a: 30 μl

30 μl of a solution with the following composition is applied into the sample-treating chamber 2a and dried.

Ascorbic acid oxidizing enzyme: 5 KU/ml

Sodium alginate: 0.2 wt % o-Phenylenediamine: 15 mM 0.1M Phosphate buffer solution: pH 7

Volume of optical-measuring chamber 3a: 10 μl

Volume of sample-treating chamber 2b: 20 μl

20 μl of a solution with the following composition is applied into the sample-treating chamber 2b and dried.

Uricase: 100 U/ml

POD (peroxidase): 100 U/ml

Sodium alginate: 0.2 wt %

0.1M phosphate buffer solution: PH 7

Volume of optical-measuring chamber 3b: 10 μl

Procedure of measurement:

50 μl of aqueous uric acid solution was applied onto the sample-receiving port, and was drawn into the analyzing device and treated according to the following sequence. The wavelength of the light beam to be measured was 440 nm.

Liquid feeding sequence:

| Step | A1 | B1 | C1 | D1 | E1 | F1 |
|---|---|---|---|---|---|---|
| Operation time (sec) | 6 | 30 | 6 | 90 | 2 | — |
| Suction rate (μl/sec) | 5 | At rest | 2 | At rest | 5 | At rest |

NOTE:
A1: Sample is introduced into the sample-treating chamber 2a.
B1: Ascorbic acid is decomposed for 30 seconds.
C1: Sample is introduced into the optical-measuring chamber 3a and the sample-treating chamber 2b.
D1: Sample blank value is determined in the optical-measuring chamber 3a, and then in the sample-treating chamber 2b color generation reaction is performed.
E1: Reaction liquid is introduced into the optical-measuring chamber 3b.
F1: Optical density of the treated liquid is measured.

Results of measurement:

| Aqueous Uric acid solution | No. of measurements | OD | Standard deviation | Coefficient of variation (%) |
|---|---|---|---|---|
| 3 mg/dl | 5 | 0.445 | 0.008 | 3.2 |
| 8 mg/dl | 5 | 0.850 | 0.014 | 2.1 |

NOTE:
OD: Optical density
Average of difference (OD3b − CD3a) between the sample blank value (OD3a) in optical-measuring chamber 3a and the light-measured value (OD3b) in optical-measuring chamber 3b.

Conclusion:

By using the biological fluid analyzing device of this invention, reliable results, low in standard deviation and coefficient of variation, were obtained.

(EXAMPLE 2)

Measurement of glucose in blood

By using the analyzing device of FIG. 3, measurement was taken of glucose in blood.

Sizes of regions in the analyzing device and reagents used:

Height of pathway and chambers region: 100 μm

Volume of sample-treating chamber 2a: 30 μl

30 μl of a solution with the following composition is applied into the sample-treating chamber 2a and dried.

Ascorbic acid oxidizing enzyme: 5 KU/ml

NAD: 7.2 wt %

WST-3 (produced by Dojindo Laboratories): 10.5 wt % [2-(4-iodophenyl)-3-(2,4-dinitrophenyl)-5-(2,4-disulfophenyl)-2H-tetrazolium]polyvinylpyrrolidone 0.2 wt %

0.1M phosphate buffer solution: pH 7.5

Volume of sample-treating chamber 2b: 20 μl

A solution (20 μl) having the following composition was applied to the sample-treating chamber 2b and dried.

Glucose dehydrogenase: 4 KU/ml

Diaphorase: 2 KU/ml

Polyvinylpyrrolidone: 0.2 wt %

0.1M Phosphate buffer solution: pH 7.5

Procedure of measurement:

The glucose concentration in plasma was measured by a hexokinase-glucose b-phosphate dehydrogenase ultraviolet method.

50 μl of plasma that was extracted by centrifuging whole blood was applied onto the sample-receiving port 1, and was drawn into the analyzing device and treated according to the following sequence. The wavelength of the light beam to be measured was 560 nm.

Liquid feeding sequence:

| Step | A2 | B2 | C2 | D2 | E2 | F2 |
|---|---|---|---|---|---|---|
| Operation time (sec) | 6 | 30 | 6 | 120 | 2 | — |
| Suction rate (μl/sec) | 5 | At rest | 5 | At rest | −5 | At rest |

NOTE:
A negative number of the suction rate represents a reverse feeding of sample.
A2: Sample is introduced into the sample-treating chamber 2a.
B2: Ascorbic acid in the sample is decomposed.
C2: Sample is introduced into the optical-measuring chamber 3a and the sample-treating chamber 2b.
D2: Sample blank value is measured in the optical-measuring chamber 3a and at the same time the sample is treated in the sample-treating chamber 2b.
E2: A part of the reaction liquid in the sample-treating chamber 2b is returned under pressure to the optical-measuring chamber 3a.
F2: Optical density of the treated liquid is measured.

Results of measurement:

| Glucose concentration in plasma | No. of measurements | OD | Standard deviation | Coefficient of variation (%) |
|---|---|---|---|---|
| 81 mg/dl | 5 | 0.473 | 0.004 | 2.31 |
| 300 mg/dl | 5 | 0.953 | 0.010 | 1.53 |

NOTE:
OD: Optical density
Average of difference between the sample blank value in optical-measuring chamber 3a and the measured value of treated solution.

Conclusion:

By using the biological fluid analyzing device of this invention, reliable results, low in standard deviation and coefficient of variation, were obtained.

(EXAMPLE 3)

Measurement of hemolyzed sample

In the process of measuring glucose in blood by using the analyzing device of FIG. 3, the effect that correction based on the sample blank in the optical-measuring chamber 3a has on the measurement of a hemolyzed sample was checked. The sample used is a plasma containing hemoglobin (produced by International Reagents Cooperation, "interference check"). The measurement was taken at a wavelength of 560 nm. Three measurements were taken and averaged.

Results of measurement:

| Hemoglobin concentration (mg/dl) | OD after reaction (A) | OD for sample blank (B) | A−B |
|---|---|---|---|
| 0 | 0.695 | 0.298 | 0.397 |
| 100 | 0.739 | 0.343 | 0.396 |
| 300 | 0.848 | 0.447 | 0.401 |
| 500 | 0.946 | 0.547 | 0.399 |

(Reference 1) Relationship between the polyester film thickness and optical density The relation between the thickness of red polyester film (Y), 50 μm, 100 μm, 188 μm, and optical density (X) is as follows. The wavelength at which to measure optical density is 540 nm.

$Y_{50}$ (50 μm-thick polyester film)=$115.022X_{50}$ +1.999
$\gamma$=0.9882

$Y_{100}$ (100 μm-thick polyester film)=$115.070X_{100}$ +8.483
$\gamma$=0.9880

$Y_{188}$ (188 μm-thick polyester film)=$116.532X_{188}$−1.515
$\gamma$=0.9770

Measuring instrument:

For thickness electronic micrometer: Hakattaro produced by Seiko EM

For optical density: U3210 spectrophotometer produced by Hitachi Ltd.

(EXAMPLE 4)

Measurement of uric acid in blood

The result of measurement of uric acid in blood using the analyzing device of FIG. 8 is shown below. Spacer 11 used is a red polyester film (188 μm thick).

| | | Light measuring chamber thickness not corrected | Light measuring chamber thickness corrected |
|---|---|---|---|
| Low concentration sample | Average | 3.5 | 3.5 |
| | Standard deviation | 0.89 | 0.88 |
| Number of measurements 10 | Coefficient of variation (%) | 2.8 | 2.6 |
| High concentration sample | Average | 10.4 | 10.5 |
| | Standard deviation | 0.19 | 0.16 |
| Number of measurements 10 | Coefficient of variation (%) | 1.8 | 1.3 |

The coefficient of variation of the red polyester film thickness was found to be 0.3%.

(EXAMPLE 5)

Measurement of glucose in blood

The result of measurement of glucose in blood using the analyzing device of FIG. 9 with a 150 μm-thick transparent polyester film as the adjuster 13 and a 50 μm-thick red polyester film as the spacer 11 is shown below. The measuring wavelength was 560 nm.

The hole diameter of the optical-measuring portion 14 in the adjuster 13 is 6 mm, and that 3a of the spacer 11 is 4 mm.

|  |  | Light measuring chamber thickness not corrected | Light measuring chamber thickness corrected |
|---|---|---|---|
| Low concentration sample | Average | 89.8 | 90.0 |
|  | Standard deviation | 1.98 | 1.34 |
| Number of measurements 10 | Coefficient of variation (%) | 2.2 | 1.6 |
| High concentration sample | Average | 226.1 | 226.5 |
|  | Standard deviation | 3.84 | 2.27 |
| Number of measurements 10 | Coefficient of variation (%) | 1.7 | 1.1 |

The coefficient of variation of the red polyester film thickness used as a spacer was found to be 0.7%.

(EXAMPLE 6)

Effect of oxygen supply

A sample-treating chamber of the analyzing device was applied with the following reagents and then dried. A plasma whose glucose concentration is known was applied as a sample onto the sample-receiving port and transferred to the sample-treating chamber where it was mixed with the reagents. The sample was further moved to a sample-treating chamber having an oxygen-supply capability and was reacted there for one minute. After this, the sample was fed to the optical-measuring section where its optical density was measured. For comparison, the plasma with the same glucose concentration was mixed with reagents in the sample-treating chamber and allowed to stand for one minute, rather than transferring it to the sample-treating chamber for oxygen-supply. Then the sample was moved to the optical-measuring section where its optical density was measured. This experiment uses PTFE type filter T-100A (produced by Toyo Roshi) as the gas-permeable film 17.

Figure 18:
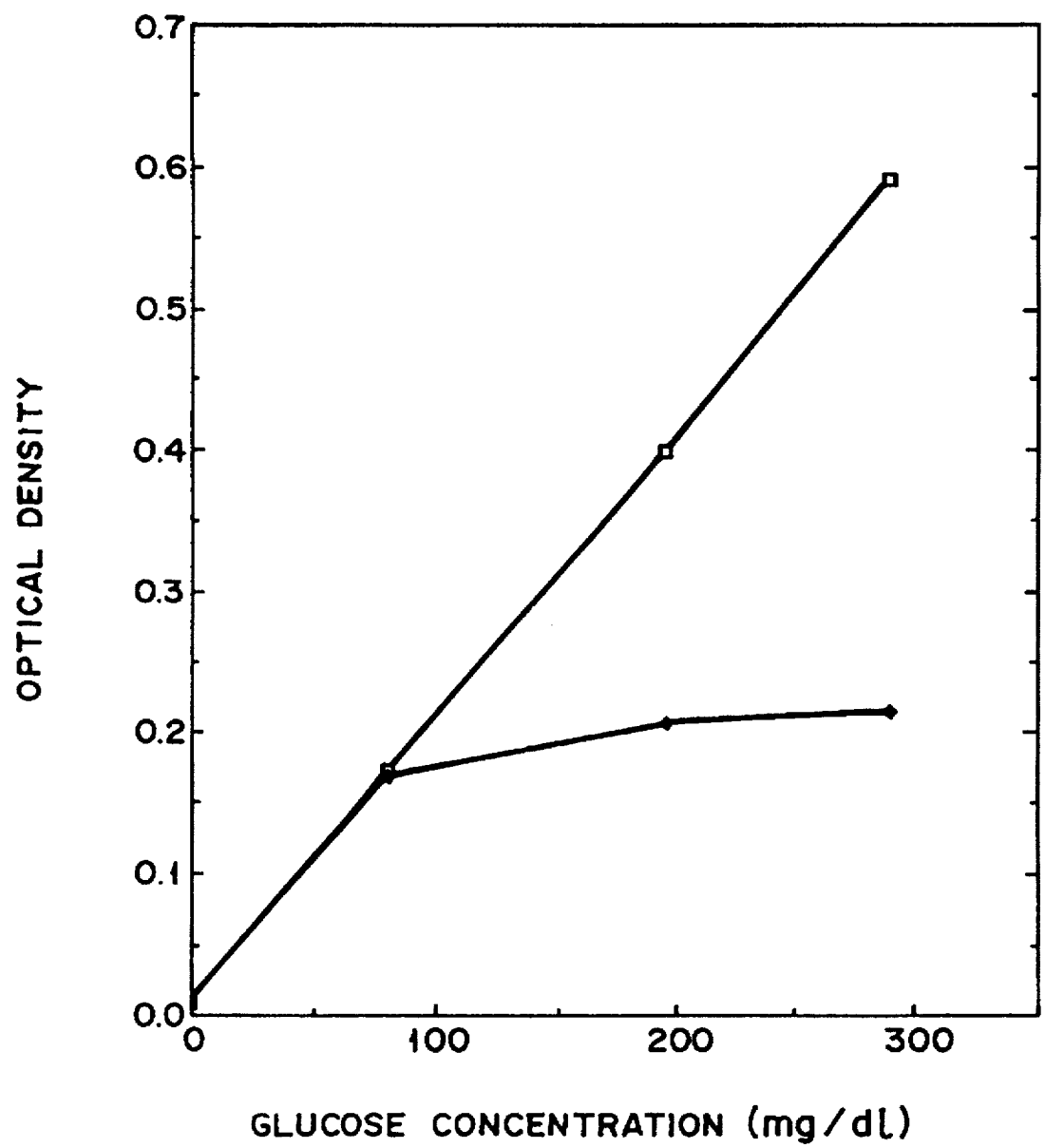
FIG. 18 is a graph showing the relationship between the concentration of glucose and the optical density representing the effectiveness of the oxygen supplying layer.

The result is shown in FIG. 18.
Prescription for reagents:
Glucose oxidase: 1800 U
Peroxidase: 1000 U
Aminoantipyrine: 20 mg
Sodium-1-naphthol-3,6-disulfonate: 30 mg
0.1M phosphate buffer solution: 1.0 ml
Results of measurement

| Glucose concentration (md/dl) | Optical density | |
|---|---|---|
|  | Oxygen supplied | Oxygen not supplied |
| 0 | 0.01 | 0.01 |
| 80 | 0.173 | 0.170 |
| 195 | 0.397 | 0.207 |
| 290 | 0.589 | 0.215 |

As shown in FIG. 18 wherein the curve 25 when the oxygen-supply treatment chamber is provided and the curve 26 shows when oxygen is not supplied, there is a lack of oxygen and the reaction is halted in the process, when the oxygen-supply treatment chamber is not used.

(EXAMPLE 7)

Comparison between plasma extracted by the analyzing device of this invention and plasma obtained by centrifugation In the analyzing device of this invention having a filter with corpuscle-separation, a sample-treating chamber was applied with triglyceride reagent and dried. The concentration of triglyceride was measured in an optical-measuring chamber. A membrane filter having inclined pores which is made of polysulfonic acid ether was used. For comparison, a plasma obtained by centrifuging the same amount of whole blood was applied directly onto the sample receiving port, which was not provided with a filter.

5 μl of reagents as prescribed below was applied onto the sample-treating chamber as the triglyceride measuring reagent and dried at 40° C. for 30 minutes.

Glyceroldehydrogenase: 1000 U
Lipoprotein lipase: 500 U
β-NAD (Nicotinamide adenine dinucleotide): 40 mg
WST-3 (produced by Dojindo Laboratories): 30 mg
0.1M HEPES buffer solution (PH 8.0): 1 ml The results of measurement of optical density are tabulated below. Five measurements were taken and averaged.

| Triglyceride concentration | Optical density | |
|---|---|---|
|  | plasma extracted by analyzing device of this invention | plasma obtained by centrifugation |
| 100 mg/dl | 0.78 | 0.79 |
| 200 mg/dl | 1.05 | 1.07 |
| 400 mg/dl | 1.63 | 1.61 |

As described above, the plasma extracted by this analyzing device exhibited a similar color to that of plasma extracted by centrifugation.

With this invention, it is possible to attain high level of precision in analyzing a liquid sample through a series of reaction and measuring steps without being affected by physical properties of the sample. It is also possible to provide a biological fluid analyzing device that allows measurements to be made easily and an analyzing method using such a device.

The invention also extends to a biological fluid analyzing device of laminar form comprising at least two layers, a fluid pathway being provided in one of the layers or partly in each of the layers or between adjacent layers, the pathway leading from a first port to a second port, the pathway affording at least two chambers along its length, at least one of the chambers being provided with at least one light passage means, e.g. a transparent wall, whereby a change in optical properties of material located in the chamber can be detected or measured from outside the device.

The chamber other than the one provided with light passage means, which is termed the treating chamber, preferably contains a reagent for treating the sample to be tested.

The reagent is preferably localized within the treating chamber, for example, by being deposited on a wall thereof.

Filter means are preferably located in the pathway adjacent one of the ports, preferably the inlet port.

The wall of at least a portion of the pathway or chambers is preferably provided by a gas permeable, liquid impermeable membrane which is in contact with a layer whereby oxygen can pass through the membrane into the pathway or chamber.

We claim:

1. A biological fluid analyzing device for analyzing biological fluid by measuring optical characteristics of a sample, comprising:
   a body comprising an upper and a lower parallel plates;
   a sample-receiving port and a pump-connection port, each defined in an outer surface of said body;
   a single fluid pathway defined between facing surfaces of said upper and lower plates, said fluid pathway fluidly connecting said sample-receiving port and said pump-connection port;
   at least one sample-treating chamber and at least one optical-measuring chamber, each chamber being defined between said facing surfaces of said upper and lower plates and each chamber defining a portion of said fluid pathway, wherein the pathway is a capillary.

2. A biological fluid analyzing device according to claim 1, wherein the body comprises an upper plate, a lower plate, an adjuster and a spacer between the upper plate and the lower plate, said adjuster being disposed between said spacer and said lower plate, said adjuster and said spacer each having through-holes therein defining a portion of at least one sample-treating chamber, at least one optical-measuring chamber and pathway, said through-holes of said adjuster defining the portion of said optical-measuring chamber being larger than the through-hole of said spacer defining the portion of the optical-measuring chamber.

3. A biological fluid analyzing device as in claim 1, wherein said fluid pathway is substantially unbranched and wherein each said chamber has a fluid inlet and a fluid outlet.

4. A biological fluid analyzing device for analyzing biological fluid by measuring optical characteristics of a sample, comprising:
   a body comprising an upper and a lower parallel plates;
   a sample-receiving port and a pump-connection port, each defined in an outer surface of said body;
   a single fluid pathway defined between facing surfaces of said upper and lower plates, said fluid pathway fluidly connecting said sample-receiving port and said pump-connection port;
   at least one sample-treating chamber and at least one optical-measuring chamber, each chamber being defined between said facing surfaces of said upper and lower plates and each chamber defining a portion of said fluid pathway; and
   at least one waste liquid reservoir chamber between the sample receiving port and the pump-connection port, and connected to said pathway.

5. A biological fluid analyzing device according to claim 1 or 4, wherein a plurality of sample-treating chambers are provided and at least one of the sample-treating chambers is provided between the optical-measuring chamber and the pump-connection port.

6. A biological fluid analyzing device according to claim 1 or 4, wherein the body includes an upper plate and a lower plate, the device further comprising a spacer between said upper and lower plates, wherein the spacer has formed therein through-holes defining portions of at least one sample-treating chamber, at least one optical-measuring chamber, and pathway, and wherein the sample-receiving port and the pump-connection port are provided in one of the upper plate and the lower plates, such that upon coupling said upper plate to said lower plate with the spacer therebetween, said at least one sample-treating chamber, said at least one optical-measuring chamber and said pathway are formed.

7. A biological fluid analyzing device according to claim 6, further comprising at least one waste liquid reservoir chamber between the sample receiving port and the pump-connection port and connected to the pathway, a portion of said waste liquid reservoir chamber being defined by a through-hole in the spacer.

8. A biological fluid analyzing device according to claim 1 or 4, wherein said body comprises an upper plate and a lower plate, said upper plate being provided with the sample-receiving port and the pump-connection port, and one of the upper plate and the lower plate being provided with at least one sample-treating chamber, at least one optical-measuring chamber and pathway, such that upon coupling said upper plate to said lower plate, said at least one sample-treating chamber, said at least one optical-measuring chamber and said pathway are formed.

9. A biological fluid analyzing device according to claim 8, wherein at least a portion of the upper plate forming the optical-measuring chamber is light-reflective and at least a portion of the lower plate forming the optical-measuring chamber is light-transmissive.

10. A biological fluid analyzing device according to claim 8, wherein at least a portion of the upper plate forming the optical-measuring chamber is light-transmissive and at least a portion of the lower plate forming the optical-measuring chamber is light-reflective.

11. A biological fluid analyzing device according to claim 8, wherein at least portions of the upper plate and the lower plate forming the optical-measuring chamber are light-transmissive.

12. A biological fluid analyzing device according to claim 8, further comprising an optical characteristic correction reference region in the body.

13. A biological fluid analyzing device according to claim 12, wherein at least a portion of the upper plate defining the optical-measuring chamber and/or the optical characteristic correction reference region is light-reflective, and at least a portion of the lower plate defining the optical-measuring chamber and/or the optical characteristic correction reference region is light-transmissive.

14. A biological fluid analyzing device according to claim 12, wherein at least a portion of the upper plate defining the optical-measuring chamber and/or the optical characteristic correction reference region is light-transmissive, and at least a portion of the lower plate defining the optical-measuring chamber and/or the optical characteristic correction reference region is light-reflective.

15. A biological fluid analyzing device according to claim 12, wherein at least portions of the upper plate and the lower plate defining the optical-measuring chamber and/or the optical characteristic correction reference region are optically-transmissive.

16. A biological fluid analyzing device for analyzing biological fluid by measuring optical characteristics of a sample, comprising:
   a body comprising an upper and a lower parallel plates;
   a sample-receiving port and a pump-connection port, each defined in an outer surface of said body;
   a single fluid pathway defined between facing surfaces of said upper and lower plates, said fluid pathway fluidly connecting said sample-receiving port and said pump-connection port;
   at least one sample-treating chamber and at least one optical-measuring chamber, each chamber being defined between said facing surfaces of said upper and lower plates and each chamber defining a portion of said fluid pathway, wherein said body comprises an upper plate and a lower plate, said upper plate being provided with the sample-receiving port and the pump-connection port, and one of the upper plate and the lower plate being provided with at least one sample-treating chamber, at least one optical-measuring chamber and pathway, such that upon coupling said upper plate to said lower plate, said at least one sample-treating chamber, said at least one optical-measuring chamber and said pathway are formed; and further comprising at least one waste liquid reservoir chamber between the sample-receiving port and the pump-connection port and connected to the pathway, wherein the at least one sample-treating chamber, at least one optical-measuring chamber, pathway and at least one waste liquid reservoir are each provided in the lower plate.

17. A biological fluid analyzing device for analyzing biological fluid by measuring optical characteristics of a sample, comprising:

a body comprising an upper and a lower parallel plates;

a sample-receiving port and a pump-connection port, each defined in an outer surface of said body;

a single fluid pathway defined between facing surfaces of said upper and lower plates, said fluid pathway fluidly connecting said sample-receiving port and said pump-connection port;

at least one sample-treating chamber and at least one optical-measuring chamber, each chamber being defined between said facing surfaces of said upper and lower plates and each chamber defining a portion of said fluid pathway;

wherein a gas-permeable film and an air layer isolated by the gas-permeable film are provided in the at least one sample-treating chamber.

18. A biological fluid analyzing device for analyzing biological fluid by measuring optical characteristics of a sample, comprising:

a body comprising an upper and a lower parallel plates;

a sample-receiving port and a pump-connection port, each defined in an outer surface of said body;

a single fluid pathway defined between facing surfaces of said upper and lower plates, said fluid pathway fluidly connecting said sample-receiving port and said pump-connection port;

at least one sample-treating chamber and at least one optical-measuring chamber, each chamber being defined between said facing surfaces of said upper and lower plates and each chamber defining a portion of said fluid pathway; and a blood corpuscle-separating portion in the form of a filter through which blood corpuscles cannot pass disposed adjacent the sample-receiving port and securely held at its outer periphery by a retaining portion defined in the body.

19. A biological fluid analyzing device according to claim 18, wherein the pathway is formed with an air hole at a point downstream of the filter.

20. A blood corpuscle separating method using the biological fluid analyzing device according to claim 18 or 19, wherein whole blood, after having been applied onto the sample-receiving port, is drawn into the body by suction from the pump-connection port.

21. A biological fluid analyzing device of laminar form comprising at least two adjacent generally parallel layers, a single fluid pathway being defined between the adjacent layers, the fluid pathway leading between and fluidly coupling a first port and a second port, the fluid pathway being in flow communication with at least first and second chambers along its length, at least said first chamber being provided with at least one light passage means, whereby a change in optical properties of material located in said first chamber can be measured from outside the device; wherein a wall of at least a portion of the pathway and the chambers is a gas permeable liquid impermeable membrane which is in contact with an air layer, whereby oxygen can pass through the membrane into the pathway or chamber.

22. A biological fluid analyzing device as in claim 21, wherein said fluid pathway is substantially unbranched and wherein each said chamber has a fluid inlet and a fluid outlet.

23. A device as claimed in claim 21, wherein the second chamber contains a reagent for treating the material to be tested.

24. A device as claimed in claim 23, wherein the reagent is localized within the second chamber.

25. A device as claimed in claim 21, 23 or 24, wherein filter means are located in the said pathway adjacent one of the ports.

* * * * *